United States Patent [19]

Poss et al.

[11] Patent Number: 5,631,372
[45] Date of Patent: May 20, 1997

[54] PROCESS FOR THE MANUFACTURE OF 1-SUBSTITUTED-4-FLUORO-1,4-DIAZONIABICYCLO[2.2.2] OCTANE SALTS

[75] Inventors: Andrew J. Poss, Kenmore; George A. Shia, Amherst; Dennis M. Lavery, Springville, all of N.Y.

[73] Assignee: AlliedSignal Inc., Morris Township, N.J.

[21] Appl. No.: 642,994

[22] Filed: May 6, 1996

Related U.S. Application Data

[60] Continuation-in-part of Ser. No. 477,038, Jun. 7, 1995, which is a division of Ser. No. 173,297, Dec. 23, 1993, Pat. No. 5,459,267.

[51] Int. Cl.$^6$ .................... C07D 247/00; C07D 245/04; C07D 243/14; C07F 9/06
[52] U.S. Cl. .................... 544/352; 544/337; 540/472; 540/542; 540/567
[58] Field of Search .................... 544/352, 337; 540/472, 542, 567

[56] References Cited

U.S. PATENT DOCUMENTS

| | | | |
|---|---|---|---|
| 3,038,903 | 6/1962 | Farkas et al. | 260/268 |
| 4,973,697 | 11/1990 | Umemoto et al. | 546/295 |
| 5,086,178 | 2/1992 | Banks | 544/351 |
| 5,367,071 | 11/1994 | Syvret | 540/472 |

FOREIGN PATENT DOCUMENTS 0478210  4/1992  European Pat. Off. .

OTHER PUBLICATIONS

Banks et al., 1–Alkyl–4–fluoro–1,4–diazoniabicyclo[2.2.2] octane Salts: a Novel Family of Electrophilic Fluorinating Agents, *J. Chem. Soc., Chem. Commun., Jan. 29, 1992*, p. 595.

Farkas et al., "Some Derivatives of 1,4–Diazabicyclo (2.2.2)octane (Triethylenediamine)", *J. Chem. Eng. Data*, vol. 13, No. 2, Apr. 1968.

Lal, "Site–Selective Fluorination of Organic Compounds Using 1–Alkyl–4–fluoro–1,4–diazabicyclo[2.2.2]octane Salts (Selectfluor Reagents)," *J. Org. Chem.* 1993, 58, 2791–2796.

Murtagh, V., "Electrophilic Fluorination: An Introduction," *Performance Chemicals*, Aug./Sep. 1991, p. 36.

Umemoto et al., "N–Fluoropyridinium Triflate and Its Analogs, The First Stable 1:1 Salts of Pyridine Nucleus and Halogen Atom" *Tetrahedron Letters*, vol. 27, No. 28 (1986), pp. 3271–3274.

Gilicinski et al., "On the relative power of electrophilic fluorinating reagents of the N–F class," *J. Fluorine Chemistry*, 59, (1992) 157–162.

Organic Chemistry, Third Edition, R.T. Morrison and R.N. Boyd, p. 751.

*Primary Examiner*—Johann Richter
*Assistant Examiner*—Jane C. Oswecki
*Attorney, Agent, or Firm*—Jay P. Friedenson

[57] ABSTRACT

A process for producing 1-substituted-4-fluoro-1,4-diazoniabicyclo[2.2.2]octane salts having the formula

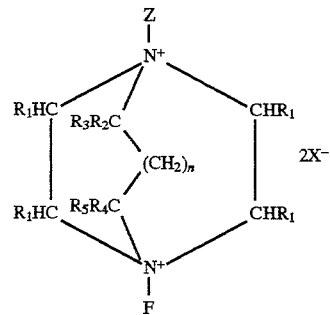

wherein the Z substituent is OH, OR, OC(O)R, SO$_3$, SO$_2$R, NO$_2$, NO, or PO(OR)$_2$, wherein R is an aryl or C$_1$–C$_8$ alkyl group; n is 0, 1 or 2; each of R$_1$, R$_2$, R$_3$, P$_4$ and R$_5$ independently represent hydrogen, C$_1$ to C$_8$ alkyl, or aryl 1-substituted-1,4-diazoniabicyclo[2.2.2]octane or 1,4-diazoniabicyclo[2.2.2]octane mono-N-oxide is reacted to attach the Z group and then the result is reacted with molecular fluorine in the presence of a solvent that substantially does not react with fluorine and a fluoride scavenger that results in an X counter ion. These compounds are useful as fluorinating agents for the introduction of fluorine into organic compounds.

20 Claims, No Drawings

PROCESS FOR THE MANUFACTURE OF 1-SUBSTITUTED-4-FLUORO-1,4-DIAZONIABICYCLO[2.2.2] OCTANE SALTS

CROSS REFERENCE TO RELATED APPLICATIONS

This application is a continuation-in-part of copending U.S. patent application Ser. No. 08/477,038, filed Jun. 7, 1995 which is a divisional of U.S. patent application Ser. No. 08/173,297 filed Dec. 23, 1993, now U.S. Pat. No. 5,459,267, which is incorporated herein by reference.

FIELD OF THE INVENTION

The present invention pertains to a method for the preparation of 1-substituted-4-fluoro-1,4-diazoniabicyclo[2.2.2] octane salts. These compounds are useful as fluorinating agents for organic compounds.

DESCRIPTION OF THE PRIOR ART

It is known in the art that fluorinating agents having a structure containing an N—F bond are stable, easily handled reagents capable offluorinating organic molecules. In this regard, see Murtage, Perform. Chem. (1991)6, 36 and (1992)7, 27 and U.S. Pat. No. 4,973,697. Fluorinating agents of the 1-alkyl-4-fluoro-1,4-diazoniabicyclo[2.2.2]octane salt type have been formed from 1,4-diazoniabicyclo[2.2.2]octane salts as disclosed in U.S. Pat. No. 5,086,178 and in J. Chem. Soc. Chem. Commun. (1992) 595 as well as by Lal in J. Org. Chem. (1993) 58, 2791. To produce the 1-alkyl-4-fluoro-1,4-diazoniabicyclo[2.2.2]octane salts, the patentee of U.S. Pat. No. 5,086,178 forms a nitrogen-carbon (N—C) bond with the nitrogen at position 1 of the tricyclic ring system. The 1-substituent is a quaternizing organic group which forms the N—C bond to make the nitrogen at the 1 position a quaternary nitrogen. A process for preparing difluorinated diazoniabicycloalkane derivatives is disclosed in U.S. Pat. No. 5,367,071. All of the foregoing are incorporated herein by reference.

It has now been found that inorganic substituents other than quaternizing organic groups can be achieved at the 1 position nitrogen of 1-substituted-4-fluoro-1,4-diazoniabicyclo[2.2.21]octane salts which forms the N—C bond. The fluorinating agents of this invention do not form a quaternized N—C bond. They employing such groups as —OH, —OR and —OC(O)R which are advantageous since these groups are more electronegative than the N—C forming quaternizing groups. The greater the electronegativity of the group affecting the N—F bond, the greater the ease of electrophilic fluorine transfer. The presence of the preferred highly electronegative groups leads to extremely powerful fluorinating agents. The fluorination reactivity of the inventive compounds is better since lower reaction temperatures are needed, they are more stereospecific in the fluorination ofenol ethers and more regiospecific in the fluorination of naphthols. The fluorinating agent which has an OH group has the advantages of enhanced electronegativity, ease of preparation and decreased manufacturing costs.

SUMMARY OF THE INVENTION

The invention provides a process for the preparation of 1-substituted-4-fluoro-1,4-diazoniabicyclo[2.2.2]octane salts having the Formula I:

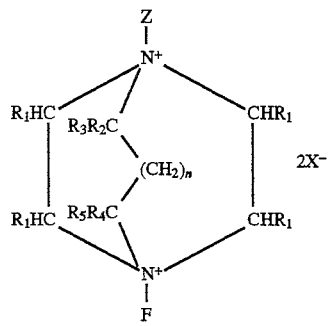

wherein the Z substituent is OH, OR, OC(O)R, $SO_3$, $SO_2R$, $NO_2$, NO, or $PO(OR)_2$, wherein R is an aryl or $C_1$–$C_8$ alkyl group; n is 0, 1 or 2; each of $R_1$, $R_2$, $R_3$, $R_4$ and $R_5$ independently represent hydrogen, $C_1$ to $C_8$ alkyl, or aryl, which process comprises (a) either (i) or (ii):
  (i) reacting 1,4-diazoniabicyclo[2.2.2]octane with a reactant compound of the formula, L—$SO_2R$, $HNO_2$, $HNO_3$, or L—$PO(OR)_2$; or
  (ii) reacting 1,4-diazoniabicyclo[2.2.2]octane mono-N-oxide with a reactant compound of the formula L—H, L—R, L—C(O)R or $SO_3$ to produce an intermediate having the Formula II:

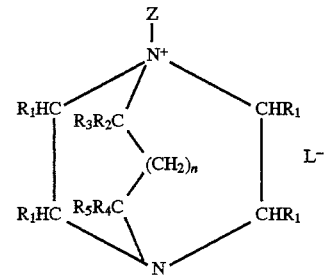

wherein L is a leaving group;

(b) exchanging the leaving group L, from step (a) with an anion X which is selected from the group consisting of fluorosulfate ($SO_3F^-$), alkyl sulfates, perfluoroalkylsulfonates, arenesulfonates, alkylcarboxylates, perfluoroalkylcarboxylates, tetrafluoroborate ($BF_4^-$), tetraphenylborate ($Ph_4B^-$), hexafluorophosphate ($PF_6^-$), hexafluoroantimonate ($SbF_6^-$), perchlorate ($ClO_4^-$) and sulfate ($SO_4^-$=$2X^-$); and (c) reacting the result from step (b) with molecular fluorine in the presence of a solvent that does not react substantially with fluorine and a fluoride scavenger that results in an X counter ion.

DETAILED DESCRIPTION OF THE PREFERRED EMBODIMENT

In general, the invention presents a method for the preparation of 1-substituted-4-fluoro-1,4-diazoniabicyclo[2.2.2] octane salts having the above Formula I. The substituent groups represented by Z in the method of this invention have nitrogen-heteroatom (N—Z) bonds and are the result of oxidation of the nitrogen atom. These substituent Z groups may be: OH, OR, OC(O)R, $SO_3$, $SO_2R$, $NO_2$, NO, PO(O)(OR)$_2$, with R being an aryl or $C_1$–$C_8$ alkyl group. It is preferred that all $R_1$ are hydrogen and usually no more than one of $R_2$, $R_3$, $R_4$ and $R_5$ is other than hydrogen. When any of $R_1$ to $R_5$ is other than hydrogen, it is preferably benzyl, phenyl or, especially, $C_1$-$C_4$ alkyl, particularly methyl. Due to steric considerations it is not possible to obtain compounds of this formula with all possible combinations of $R_1$ to $R_5$ values. Usually no more than one $R_1$ at the 2 and 3 ring positions and no more than one $R_1$ at the 5 and 6 positions will be other than hydrogen.

In the first step (a) of producing the compounds of this invention, 1,4-diazoniabicyclo[2.2.2]octane is reacted with a compounnd of the formula L—$SO_2$R, $HNO_2$, $HNO_3$, or L—PO(OR)$_2$. Non-exclusive examples of useful compounds of the formulae L—$SO_2$R, $HNO_2$, $HNO_3$, or L—PO(OR)$_2$ are methanesulfonyl chloride, phenylsulfonyl chloride, chlorophosphonic acid diethyl ester and diphenyl chlorophosphate. Alternatively, 1,4-diazoniabicyclo[2.2.2] octane mono-N-oxide is reacted with a compound of the formula L—H, L—R, L—C(O)R or $SO_3$, wherein L is a leaving group, to produce an intermediate of Formula II. For the purposes of this invention, a leaving group is a stable species that can be detached from a molecule during a reaction. Non-exclusive examples of useful compounds of the formulae L—H, L—R, L—C(O)R or $SO_3$ are fluoroboric acid, iodomethane and acetyl chloride. 1,4-diazoniabicyclo[2.2.2]octane N-oxide may be prepared by the hydrogen peroxide oxidation oftriethylenediamine in water. Step (a) is conducted by reacting one equivalent of either 1,4-diazoniabicyclo[2.2.2]octane or 1,4-diazoniabicyclo[2.2.2]octane mono-N-oxide with from about 1 to about 2, or more preferably from about 1 to about 1.25 equivalents of its respective reagent to produce the intermediate of Formula II. The step (a) reaction may be conducted at a temperature of from about –40° C. to about 25° C., preferably from about 10° C. to about 25° C. and more preferably from about 15° C. to about 20° C. The reaction may be conducted by dispersing the reagents in an excess of a suitable solvent such as an organic solvent, water or mixtures thereof. Preferred organic solvents include diethyl ether, dibutyl ether, dipropyl ether, glyme, 1,2-dichloroethane, tetrahydrofuran, methylene chloride, dimethoxyethane, acetonitrile, propionitrile, chloroform, trichlorofluoromethane, trichlorofluoroethane, 1,1,2,2-tetrachloroethane and mixtures thereof.

In step (b) the leaving group L of the intermediate of Formula II is then exchanged with an anion X. Each X— independently represents a counterion or 2X—represents a single divalent counterion. Preferably X is selected from the group consisting of fluorosulfate ($SO_3$ F$^-$), alkyl sulfates, perfluoroalkylsulfonates, arenesulfonates, alkylcarboxylates, perfluoro-alkylcarboxylates, tetrafluoroborate ($BF_4^-$), tetraphenylborate ($Ph_4B^-$), hexafluorophosphate ($PF_6^-$), hexafluoroantimonate ($SbF_6^-$), perchlorate ($ClO_4^-$) and sulfate ($SO_4^-$=2X$^-$). The most preferred anion is tetrafluoroborate. The anion X can originate from such compounds as sodium tetrafluoroborate, fluoroboric acid, tetrafluoroboric acid, boron trifluoride gas, boron trifluoride etherate and boron trifluoride-acetonitrile complex. As an example, the preferred $BF_4^-$ can originate from one equivalent of sodium tetrafluoroborate and one equivalent of fluoroboric acid; two equivalents of sodium tetrafluoroborate; one equivalent of tetrafluoroboric acid and an equivalent of boron trifluoride etherate; one equivalent of tetrafluoroboric acid and an equivalent of boron trifluoride gas; or two equivalents of boron trifluoride gas and an equivalent of water. Step (b) is conducted by reacting one equivalent of the intermediate of Formula II with from about 1 to about 2, or more preferably from about 1 to about 1.25 equivalents of the compound having the X anion. This reaction step may be conducted at a temperature of from about –40° C. to about 25° C., preferably from about 10° C. to about 25° C. and more preferably from about 15° C. to about 20° C. The reaction may be conducted by dispersing the reagents in an excess of a suitable solvent such as an organic solvent, water or mixtures thereof. Preferred organic solvents include tetrahydrofuran, methylene chloride, dimethoxyethane, acetonitrile, propionitrile, chloroform, trichlorofluoromethane, trichlorofluoroethane and mixtures thereof.

Step (c) may be conducted by reacting the result from step (b) with molecular fluorine in the presence of a solvent that substantially does not react with fluorine and a fluoride scavenger that results in an X counter ion. Suitable solvents non-exclusively include organic solvents, water or mixtures thereof. Preferred organic solvents include acetonitrile, propionitrile, trichlorofluoromethane, carbon tetrachloride, trichlorofluoroethane, perchlorofluoroalkanes such as 1,1,2-trichloro-1,2,2-trifluoroethane and mixtures thereof. This reaction may be conducted at a temperature of from about –40° C. to about 25° C., preferably from about 10° C. to about 25° C. and more preferably from about 15° C. to about 20° C. Suitable fluoride scavengers non-exclusively include Lewis acids that readily react with fluoride such as aluminum trifluoride, antimony pentafluoride, arsenic pentafluoride, boron trifluoride, tris(trifluoromethyl)boron, tris(trifluorophenyl)boron, niobium pentafluoride, phosphorus pentafluoride, selenium trioxide, sulfur trioxide, tantalum pentafluoride, tellurium hexafluoride, titanium tetrafluoride, vanadium pentafluoride and zirconium tetrafluoride; also salts or silyl derivatives of alkyl sulfonates, perfluoroalkanesulfonates, arenesulfonates, alkylcarboxylates and perfluoro alkylcarboxylates such as sodium triflate and trimethylsilylacetate. The fluoride scavenger is preferably present in an amount of from about 1 equivalent to about 5 equivalents, more preferably from about 1 equivalent to about 2 equivalents and most preferably from about 1 equivalent to about 1.25 equivalents based on the amount of the intermediate of Formula II.

The reaction product is worked up by methods shown in the examples that follow. This procedure has the advantage that it can be done in three separate reactors and produces solutions that can be stored for extended periods of time. Alternatively, these compounds have the manufacturing advantage that the entire preparation can be conducted in "one pot" with water as the solvent. The use of the "one pot" procedure has the advantage of avoiding the manufacturing costs associated with multi-reactor processes and the safety problems associated with handling intermediates. The particular substituent groups of this invention are preferred since they offer a simplified and economical method of preparation for forming desirable fluorinating agents. The fluorinating reagents of this invention can be used for the fluorination of steroidal dienol acetates, eneamides, aromatics and olefins; for example, 3,5-pregndien-3,21-diol-20-one diacetate, acetanilide, phenylurethan, a-methylstyrene, anisole and phenol.

The following non-limiting examples serve to illustrate the invention.

EXAMPLE 1

1-hydroxy-4-fluoro-1,4-diazoniabicyclo[2.2.2]octane bis (tetrafluoro-borate), NFTh, from 1,4-diazoniabicyclo[2.2.2] octane N-oxide, 1 equivalent of sodium tetrafluoroborate and 1 equivalent of tetrafluoroboric acid. 1,4-Diazoniabicyclo[2.2.2]octane N-oxide was prepared by the reaction of 1,4-diazoniabicyclo[2.2.2]octane with hydrogen peroxide as described by Farkas in J. Chem. Eng. Data (1968) 13, 278. A solution of 1,4-diazoniabicyclo[2.2.2] octane N-oxide (1.28 g, 10 mmole), sodium tetrafluoroborate (1.1 g, 10 mmole), and tetrafluoroboric acid (50% solution, 1.83 g, 10 mmole) in acetonitrile (250 mL) was cooled to −35° C. and treated with a mixture of fluorine in nitrogen (10% V/V, 14 mmole). The reaction was evaporated, the remaining solid washed with acetone and dried to afford 1.23 grams of 1-hydroxy-4-fluoro-1,4-diazoniabicyclo[2.2.2]octane bis(tetrafluoroborate) (38% yield); decomposes at 125° C.; $^1$H NMR (D$_2$O): δ5.0 (m, 6H), 4.6 (m, 6H); $^{13}$C NMR (D2O): δ61.6 (d, J=15.5 Hz), 62.3 (d, J=6.2 Hz); $^{19}$F (D$_2$O): δ41(1F), −150(8F); $^{15}$N (D$_2$O): δ−207.5(d, J=84 Hz), −275.9. Anal. Calcd for C$_6$H$_{13}$B$_2$F$_9$N$_2$O: C, 22.40; H, 4.07; N, 8.70; B, 6.72. Found: C, 22.69; H, 4.25; N, B8.80; B, 6.39.

EXAMPLE 2

1-hydroxy-4-fluoro-1,4-diazoniabicyclo[2.2.2]octane bis (tetrafluoroborate), NFTh, from 1,4-diazoniabicyclo[2.2.2] octane N-oxide, 1 equivalent of boron trifluoride etherate and 1 equivalent of tetrafluoroboric acid. A solution of 1,4-diazoniabicyclo[2.2.2]octane N-oxide (2.56 g, 20 mmole), boron trifluoride etherate (2.4 mL, 20 mmole), and tetrafluoroboric acid (50% solution, 3.66 g, 20 mmole) in acetonitrile (250 mL) was cooled to 8° C. and treated with a mixture of fluorine in nitrogen (10% V/V, 52 mmole). The reaction was evaporated, the remaining solid washed with acetone and dried to afford 4.8 grams of 1-hydroxy-4-fluoro-1,4-diazoniabicyclo[2.2.2]octane bis(tetrafluoroborate) (75% yield).

EXAMPLE 3

1-hydroxy-4-fluoro-1,4-diazoniabicyclo[2.2.2]octane bis (tetrafluoroborate), NFTh, from 1,4-diazoniabicyclo[2.2.2] octane N-oxide and 2 equivalents of sodium tetrafluoroborate. A solution of 1,4-diazoniabicyclo[2.2.2]octane N-oxide (1.26 g, 9.8 mmole) and sodium tetrafluoroborate (1 g, 9.1 mmole) in acetonitrile (250 mL) was cooled to 8° C. and treated with a mixture of fluorine in nitrogen (10% V/V, 30 mmole). The reaction was evaporated, the remaining solid washed with acetone and dried to afford 1.03 grams of 1-hydroxy-4-fluoro-1,4-diazoniabicyclo[2.2.2]octane bis (tetrafluoroborate) (70% yield).

EXAMPLE 4

1-hydroxy-4-fluoro-1,4-diazoniabicyclo[2.2.2]octane bis (tetrafluoroborate), NFTh, from 1,4-diazoniabicyclo[2.2.2] octane N-oxide, 2 equivalents of boron trifluoride gas and 1 equivalent of water. A solution of 1,4-diazoniabicyclo[2.2.2] octane N-oxide (12.8 g, 0.1 mole), water (1.8 mL, 0.1 mole) and boron trifluoride (13.6 g, 0.2 mole) in acetonitrile (250 mL) was cooled to 8° C. and treated with a mixture of fluorine in nitrogen (10% V/V, 0.2 mole). The reaction was evaporated, the remaining solid washed with acetone and dried to afford 22 grams of 1-hydroxy-4-fluoro-1,4-diazoniabicyclo[2.2.2]octane bis(tetrafluoro-borate) (68% yield).

EXAMPLE 5

1-hydroxy-4-fluoro-1,4-diazoniabicyclo[2.2.2]octane bis (tetrafluoroborate), NFTh, from 1,4-diazoniabicyclo[2.2.2] octane N-oxide, 1 equivalent of boron trifluoride and 1 equivalent of tetrafluoroboric acid. A solution of 1,4-diazoniabicyclo[2.2.2]octane N-oxide (12.8 g, 0.1 mole), boron trifluoride gas (6.8 g, 0.1 mole), and tetrafluoroboric acid (50% solution, 12 g, 0.1 mole) in acetonitrile (200 mL) was cooled to 8° C. and treated with a mixture of fluorine in nitrogen (10% V/V, 0.15 mole). The reaction was evaporated, the remaining solid washed with acetone and dried to afford 21 grams of 1-hydroxy-4-fluoro-1,4-diazoniabicyclo[2.2.2]octane bis(tetrafluoroborate) (65% yield).

EXAMPLE 6

1-hydroxy-4-fluoro-1,4-diazoniabicyclo[2.2.2]octane bis (tetrafluoroborate), NFTh, from 1,4-diazoniabicyclo[2.2.2] octane N-oxide, 1 equivalent of boron trifluoride and 1 equivalent of tetrafluoroboric acid. To a solution of 1,4-diazoniabicyclo[2.2.2]octane (336 grams, 3 moles) in water (750 mL) is added 30% hydrogen peroxide (384 grams), while allowing the exotherm to raise the temperature of the reaction. The solution is refluxed for 1 hour and 830 mL of water removed by distillation. The remaining solution is heated at 85° C. for four hours, acetonitrile (300 mL) is added at that temperature and the reaction allowed to cool to room temperature. Next, 50% tetrafluoroboric acid (300 mL) is added to give 1088 g of protonated N-oxide solution.

The protonated N-oxide solution (363 grams) is added to a mixture of boron trifluoride (85 grams, 1.25 mole) in acetonitrile (900 mL) and cooled to 5° C. The reaction mixture is then treated with 47.5 grams (or 1.25 mole) of a mixture of fluorine in nitrogen (10–15% vol/vol) while maintaining the temperature between 5° and 15° C.

Next, 825 mL of solvent is distilled off (pot temperature of 80°–100° C.) at reduced pressure (50 torr) and 1,2-dimethoxyethane (450 mL) added to precipitate out all solid material. The resulting slurry is filtered and dried under vacuum to afford 255 g of NFTh (80% yield).

EXAMPLE 7

Example 6 is repeated except $^{18}$F enriched fluorine gas is substituted for the F$_2$ to afford $^{18}$F-1-hydroxy-4-fluoro-1,4-diazonia-bicyclo[2.2.2]octane bis(tetrafluoroborate).

EXAMPLE 8

The procedure described in Example 5 is followed to prepare 1-fluoro-4-sulfooxy-1,4-diazoniabicyclo[2.2.2] octane tetrafluoroborate by substituting 1-sulfooxy-4-aza-1-azoniabicyclo[2.2.2]octane for 1,4-diazoniabicyclo[2.2.2] octane N-oxide. 1-Sulfooxy-4-aza-1-azoniabicyclo[2.2.2] octane can be made by the procedure described by I. J. Galpin, G. W. Kenner, and A. Marston in Bioorg. Chem. 1979, 323–32.

EXAMPLE 9

1-fluoro-4-methoxy-1,4-diazoniabicyclo[2.2.2]octane bis (tetrafluoroborate) 1,4-Diazoniabicyclo[2.2.2]octane N-oxide is prepared by the reaction of 1,4-Diazoniabicyclo [2.2.2]octane with hydrogen peroxide as described by Farkas in J. Chem. Eng. Data (1968) 13, 278. 1,4-Diazabicyclo [2.2.2]octane N-oxide (12.8 g, 10 mmol) in THF (100 mL) is reacted with iodomethane (14.1 g, 10 mmol) until the reaction is complete by TLC. The reaction is evaporated, diluted with acetonitrile (100 mL) and sodium tetrafluoroborate (40 g, 20 mmol) added. The solution is stirred overnight at room temperature and then filtered to remove all undissolved salts. The filtrate is evaporated to afford 1-methoxy-4-aza-1-azoniabicyclo[2.2.2]octane tetrafluoroborate.

A solution of 1-methoxy-4-aza-1-azoniabicyclo[2.2.2] octane tetrafluoroborate (23 g, 10 mmole) and boron trifluoride gas (6.7 g, 10 mmole) in acetonitrile (125 mL) was cooled to 8° C. and treated with a mixture of fluorine in nitrogen (10 % V/V, 12 mmole). The reaction was evaporated, the remaining solid washed with DME and dried to afford 1 -fluoro-4-methoxy- 1,4-diazoniabicyclo[2.2.2] octane bis(tetrafluoroborate).

EXAMPLE 10

1-acetoxy-4-fluoro-1,4-diazoniabicyclo[2.2.2]octane bis (tetrafluoroborate) 1,4-Diazabicyclo[2.2.2]octane N-oxide is prepared by the reaction of 1,4-diazabicyclo[2.2.2]octane with hydrogen peroxide as described by Farkas in J. Chem. Eng. Data (1968) 13,278. 1,4-Diazabicyclo[2.2.2]octane N-oxide (12.8 g, 10 mmol) in THF (100 mL) is reacted with acetyl chloride (7.9 g, 10 mmol) until the reaction is complete by TLC. The reaction is evaporated, diluted with acetonitrile (100 mL) and sodium tetrafluoroborate (40 g, 20 mmol) added. The solution is stirred overnight at room temperature and then filtered to remove all undissolved salts. The filtrate is evaporated to afford 1-acetoxy-4-aza-1-azoniabicyclo[2.2.2]octane tetrafluoroborate.

A solution of 1-acetoxy-4-aza-1-azoniabicyclo[2.2.2] octane tetrafluoroborate (25.8 g, 10 mmole) and boron trifluoride gas (6.7 g, 10 mmole) in acetonitrile (125 mL) was cooled to 8° C. and treated with a mixture of fluorine in nitrogen (10% V/V, 12 mmole). The reaction was evaporated, the remaining solid washed with dimethoxyethane and dried to afford 1-acetoxy-4-fluoro-1,4-diazoniabicyclo[2.2.2]octane bis(tetrafluoroborate).

EXAMPLE 11

1-benzoyl-4-fluoro-1,4-diazoniabicvclo[2.2.2]octane bis (tetrafluoroborate) 1,4-Diazabicyclo[2.2.2]octane N-oxide is prepared by the reaction of 1,4-diazabicyclo[2.2.2]octane with hydrogen peroxide as described by Farkas in J. Chem. Eng. Data (1968) 13, 278. 1,4-Diazabicyclo[2.2.2]octane N-oxide (12.8 g, 10 mmool) in THF (100 mL) is reacted with benzoyl chloride (14 g, 10 mmol) until the reaction is complete by TLC. The reaction is evaporated, diluted with acetonitrile (100 mL) and sodium tetrafluoroborate (40 g, 20 mmol) added. The solution is stirred overnight at room temperature and then filtered to remove all undissolved salts. The filtrate is evaporated to afford 1-benzoyl-4-aza-1-azoniabicyclo[2.2.2]octane tetrafluoroborate.

A solution of 1-benzoyl-4-aza-1-azoniabicyclo[2.2.2] octane tetrafiuoroborate (32 g, 10 mmole) and boron trifluoride gas (6.7 g, 10 mmole) in acetonitrile (125 mL) was cooled to 8° C. and treated with a mixture of fluorine in nitrogen (10 % V/V, 12 mmole). The reaction was evaporated, the remaining solid washed with DME and dried to afford 1-benzoyl-4-fluoro-1,4-diazoniabicyclo[2.2.2] octane bis(tetrafluoroborate).

EXAMPLE 12

1-Fluoro-4-sulfo-1,4-diazoniabicyclo[2.2.2]octane bis (tetrafluoroborate) 1,4-Diazabicyclo[2.2.2]octane (11 g, 10 mmol) in THF (100 mL) is reacted with chlorosulfonic acid (11.6 g, 10 mmol) until the reaction is complete by TLC. The reaction is evaporated, diluted with acetonitrile (100 mL) and sodium tetrafluoroborate (40 g, 20 mmol) added. The solution is stirred overnight at room temperature and then filtered to remove all undissolved salts. The flitrate is evaporated to afford 1-sulfo-4-aza-1-azoniabicyclo[2.2.2] octane tetrafluoroborate.

A solution of 1-sulfo-4-aza-1-azoniabicyclo[2.2.2]octane tetrafluoroborate (28 g, 10 mmole) and boron trifluoride gas (6.7 g, 10 mmole) in acetonitrile (125 mL) was cooled to 8° C. and treated with a mixture of fluorine in nitrogen (10% V/V, 12 mmole). The reaction was evaporated, the remaining solid washed with DME and dried to afford 1-fluoro-4-sulfo-1,4-diazoniabicyclo[2.2.2]octane bis (tetrafluoroborate).

EXAMPLE 13

1-Fluoro-4-methanesulfonyl-1,4-diazoniabicyclo[2.2.2] octane bis(tetrafluoroborate) 1,4-Diazabicyclo[2.2.2]octane (11 g, 10 mmol) in tetrahydrofuran (100 mL) is reacted with methanesulfonyl chloride (11.5 g, 10 mmol) until the reaction is complete by TLC. The reaction is evaporated, diluted with acetonitrile (100 mL) and sodium tetrafluoroborate (40 g, 20 mmol) added. The solution is stirred overnight at room temperature and then filtered to remove all undissolved salts. The filtrate is evaporated to afford 1-methanesulfonyl-4-aza-1-azoniabicyclo[2.2.2]octane tetrafluoroborate.

A solution of 1-methanesulfo-4-aza-1-azoniabicyclo [2.2.2]octane tetrafluoroborate (27.8 g, 10 mmole) and boron trifluoride gas (6.7 g, 10 mmole) in acetonitrile (125 mL) was cooled to 8° C. and treated with a mixture of fluorine in nitrogen (10% V/V, 12 mmole). The reaction was evaporated, the remaining solid washed with DME and dried to afford 1-fluoro-4-methanesulfonyl-1,4-diazoniabicyclo [2.2.2]octane bis(tetrafluoroborate).

EXAMPLE 14

Diethyl 1-Fluoro-4-phosphono-1,4-diazoniabicyclo [2.2.2]octane bis(tetrafluoroborate) 1,4-Diazoniabicyclo [2.2.2]octane (11 g, 10 mmol) in THF (100 mL) is reacted with diethyl chlorophosphate (17.3 g, 10 mmol) until the reaction is complete by TLC. The reaction is evaporated, diluted with acetonitrile (100 mL) and sodium tetrafluoroborate (40 g, 20 mmol) added. The solution is stirred overnight at room temperature and then filtered to remove all undissolved salts. The filtrate is evaporated to afford diethyl-1-phosphono-4-aza-1-azoniabicyclo[2.2.2]octane tetrafluoroborate.

A solution of diethyl-1-phosphono-4-aza-1-azoniabicyclo [2.2.2]octane tetrafluoroborate (33.6 g, 10 mmole) and boron trifluoride gas (6.7 g, 10 mmole) in acetonitrile (125 mL) was cooled to 8° C. and treated with a mixture of fluorine in nitrogen (10% V/V, 12 mmole). The reaction was evaporated, the remaining solid washed with DME and dried to afford diethyl 1-fluoro-4-phosphono-1,4-diazoniabicyclo [2.2.2]octane bis(tetrafluoroborate).

EXAMPLE 15

Fluorination of asteroid:

To a solution of 3,5-pregndien-3,21-diol-20-one diacetate (10 mg, 0.026 mmole) in acetonitrile (0.3 mL) was added 1-hydroxyl-4-fluoro-1,4-diazoniabicyclo[2.2.2]octane bis (tetrafluoroborate) (15 mg, 0.047 mmole 1.8 equ.) and the reaction stirred at room temperature for 15 min. The mixture was diluted with ether (2 mL), washed with water (1 mL), 10% HCl (1 mL), and sat NaHCO$_3$ (1 mL), filtered through anhydrous MgSO$_4$, and evaporated to afford 9 mg (89% yield) of a 1:2.2 mixture of 6- to 6-fluoro 4-pregnen-21-ol-3,20-dione acetate.

EXAMPLE 16

To a solution of acetanilide (135 mg, 1 mmole) in acetonitrile (2 mL) was added 1-hydroxyl-4-fluoro-1,4- diazoniabicyclo[2.2.2]octane bis(tetrafluoroborate) (354 Mg, 1.1 mmole 1.1 equ.) and the reaction stirred at 40 degree(s) C. for 6 h. The mixture was diluted with ether (2 mL), washed with water (1 mL), 10% HCl (1 mL), and sat $NaHCO_3$ (1 mL), filtered through anhydrous $MgSO_4$, and evaporated to afford 142 mg (84% yield) of a 1:2 mixture of 4- to 2-fluoroacetanilide.

EXAMPLE 17

To a solution ofphenylurethan (165 mg, 1 mmole) in acetonitrile (2 mL) was added 1-hydroxyl-4-fluoro-1,4-diazoniabicyclo[2.2.2]octane bis(tetrafluoroborate) (354 mg, 1.1 mmole 1.1 equ.) and the reaction stirred at 80 degree(s) C. for 6 h. The mixture was diluted with ether (2 mL), filtered through anhydrous $MgSO_4$, and evaporated to afford 162 mg (88% yield) of a 2.3:1 mixture of 4- to 2-fluorophenylurethan.

EXAMPLE 18

To a solution ofalpha-methylstyrene (0.13 mL, 1 mmole) and methanol (0.05 mL, 1.1 mmole) in acetonitrile (10 mL) was added 1-hydroxyl-4-fluoro-1,4-diazoniabicyclo[2.2.2]octane bis(tetrafluoroborate) (330 mg, 1.02 mmole 1.02 equ.) and the reaction stirred at room temperature for 24 h. The mixture was diluted with ether (2 mL), filtered through anhydrous $MgSO_4$, and evaporated to afford 130 mg (85% yield) of 1-fluoro-2-methoxy-2-phenylpropane.

EXAMPLE 19

To a solution of alpha-methylstyrene (0.13 mL, 1 mmole) and water (0.02 mL, 1.1 mmole) in acetonitrile (10 mL) was added 1-hydroxyl-4-fluoro-1,4-diazoniabicyclo[2.2.2]octane bis(tetrafluoroborate) (330 mg, 1.02 mmole 1.02 equ.) and the reaction stirred at room temperature for 24 h. The mixture was diluted with ether (2 mL), filtered through anhydrous $MgSO_4$, and evaporated to afford 110 mg (71% yield) of 1-fluoro-2-hydroxy2-phenylpropane.

EXAMPLE 20

To a solution of phenol (94 mg, 1 mmole) in acetonitrile (1 mL) was added 1-hydroxyl-4-fluoro-1,4-diazoniabicyclo[2.2.2]octane bis(tetrafluoroborate) (354 mg, 1.1 mmole 1.1 equ.) and the reaction stirred at 40 degree(s) C. for 5 h. The mixture was diluted with ether (2 mL), filtered through anhydrous $MgSO_4$, and evaporated to afford 90 mg (80% yield) of a 1.2:1 mixture of 4- to 2-fluorophenol.

EXAMPLE 21

To a solution of anisole (0.11 mL, 1 mmole) in acetonitrile (2 mL) was added 1-hydroxyl-4-fluoro-1,4-diazoniabicyclo[2.2.2]octane bis(tetrafluoroborate) (326 mg, 1 mmole, 1 equ.) and the reaction stirred at room temperature for 5 h. The mixture was diluted with ether (2 mL), washed with water (1 mL), 10% HCl (1 mL), and sat $NaHCO_3$ (1 mL), filtered through anhydrous $MgSO_4$, and evaporated to afford 104 mg (83% yield) of a 1:2.4 mixture of 2- to 4-fluoroanisole. Lower reaction temperatures can be used in the fluorination of aromatics with 1-hydroxyl-4-fluoro-1,4-diazoniabicyclo[2.2.2]octane bis tetrafluoroborate because it is more reactive than 1-(chloromethyl)-4-fluoro-1,4-diazoniabicyclo[2.2.2]octane bis (tetrafluoroborate). For example, when the same conditions as described in Comparative Example 22 for fluorination of anisole were used with 1-hydroxyl-4-fluoro-1,4-diazoniabicyclo[2.2.2]octane bis tetrafluoroborate, only decomposition products were observed. However, by reacting anisole with 1-hydroxyl-4-fluoro-1,4-diazoniabicyclo[2.2.2]octane bis tetrafluoroborate at room temperature for 5 hrs., the desired products are obtained.

EXAMPLE 22 (COMPARATIVE)

The reaction of anisole with 1-(chloromethyl)-4-fluoro-1,4-diazoniabicyclo[2.2.2]octane bis (tetrafluoroborate) at 40 degree(s) C. for 6 hours afforded a 1:1 mixture of 2- and 4-fluoroanisole [Banks, R. E.; et. al. J. Chem. Soc. Chem. Commun. (1992) 595].

EXAMPLE 23

1-hydroxyl-4-fluoro-1,4-diazoniabicyclo[2.2.2]octane bis tetrafluoroborate is more stereospecific than 1-(chloromethyl)-4-fluoro-1,4-diazoniabicyclo[2.2.2]octane bis (tetrafluoroborate) in the fluorination of enol ethers as evidenced by this Example versus comparative Example 24 (4-tert-butyl-1-ethoxycyclohexene to primarily cis-4-tert-butyl-2-fluorocyclohexanone). To a solution of 4-tert-butyl-1-ethoxycyclohexene (50 mg, 0.27 mmole) in acetonitrile (0.6 mL) was added 1-hydroxyl-4-fluoro-1,4-diazoniabicyclo[2.2.2]octane bis(tetrafluoroborate) (97 mg, 0.3 mmole) and the reaction stirred at 22 degree(s) C. for 6 h, then 60 degree(s) C. for 12 h. The mixture was diluted with ether (2 mL), washed in 10% HCl (2 mL), sat $NaHCO_3$ (2 mL), filtered through anhydrous $MgSO_4$, and evaporated to afford 29 mg of a 12.8:1 mixture of cis- to trans-4-tert-butyl-2-fluorocyclohexanone contaminated with 43% of 4-tert-butylcyclohexanone.

EXAMPLE 24 (COMPARATIVE)

To a solution of 4-tert-butyl-1-ethyoxycyclohexene (50 mg, 0.27 mmole) in acetonitrile (0.6 mL) was added 1-(chloromethyl)-4-fiuoro-1,4-diazoniabicyclo[2.2.2]octane bis(tetrafluoroborate) (106 mg, 0.3 mmole) and the reaction stirred at 22 degree(s) C. for 6-h, then 60 degree(s) for 12 h. The mixture was diluted with ether (2mL), washed with 10% HCl (2 mL), sat NaHCO3 (2 mL), filtered through anhydrous $MgSO_4$, and evaporated to afford 21 mg of a 3.3:1 mixture of cis- to trans-4-tert-butyl-2-fiuorocyclohexanone contaminated with 45% of 4-tert-butylcyclohexanone.

EXAMPLE 25

1-hydroxyl-4-fluoro-1,4-diazoniabicyclo[2.2.2]octane bis tetrafluoroborate is more regioselective than 1-(chloromethyl)-4-fluoro-1,4-diazoniabicyclo[2.2.2]octane bis(tetrafluoroborate) in the fluorination of napthols as evidenced by this Example versus comparative Example 26 (2-hydroxynapthalene to primarily 1-fluoro-2-hydroxynapthlene). To a solution of 2-hydroxynapthalene (72 mg, 0.5 mmole) in acetonitrile (1 mL) was added 1-hydroxyl-4-fluoro-1,4-diazoniabicyclo[2.2.2]octane bis (tetrafluoroborate) (177 mg, 0.55 mmole) and the reaction stirred at 22 degree(s) C. for 6 h. The mixture was diluted with ether (2 mL), filtered through anhydrous $MgSO_4$, and evaporated to afford 71 mg of a 16.7:6.4:1 mixture of 1-fluoro-2-hydroxynapthlene ($^{19}$F NMR-156) to 3-fluoro-2-hydroxynapthlene ($^{19}$F NMR −153) to 1,1-difluoro-2-oxo-1,2dihydronapthalene ($^{19}$F NMR −102).

EXAMPLE 26 (COMPARATIVE)

To a solution of 2-hydroxynapthalene (72 mg, 0.5 mmole) in acetonitrile (1 mL) was added 1-(chloromethyl)-4-fluoro-1,4-diazoniabicyclo[2.2.2]octane bis(tetrafluoroborate) (195 mg, 0.55 mmole) and the reaction stirred at 22 degree(s) C. for 6 h. The mixture was diluted with ether (2 mL), filtered through anhydrous MgSO$_4$, and evaporated to afford 74 mg of a 4.7:1:2.2 mixture of 1-fluoro-2-hydroxynapthlene ($^{19}$F NMR −156) to 3-fluoro-2-hydroxynapthlene ($^{19}$F NMR −153) to 1,1-difluoro-2-oxo-1,2-dihydronapthalene ($^{19}$F NMR −102). Having described the invention in detail and by reference to preferred embodiments thereof, it will be apparent that modification and variations are possible without departing from the scope of the invention defined in the appended claims.

What is claimed is:

1. A process for the preparation of 1-substituted-4-fluoro-1,4-diazoniabicyclo[2.2.2]octane salts having the formula

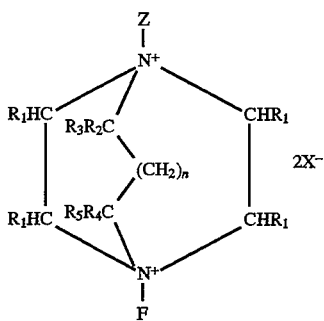

wherein the Z substituent is OH, OR, OC(O)R, SO$_3$, SO$_2$R, NO$_2$, NO, or PO(OR)$_2$, wherein R is an aryl or C$_1$–C$_8$ alkyl group; n is 0, 1 or 2; each of R$_1$, R$_2$, R$_3$, R$_4$ and R$_5$ independently represent hydrogen, C$_1$ to C$_8$ alkyl, or aryl, which process comprises (a) either (i) or (ii):
(i) reacting 1,4-diazoniabicyclo[2.2.2]octane with a reactant compound of the formula, L—SO$_2$R, HNO$_2$, HNO$_3$, or L—PO(OR)$_2$; or
(ii) reacting 1,4-diazoniabicyclo[2.2.2]octane mono-N-oxide with a reactant compound of the formula L—H, L—R, R, L—C(O)R or SO$_3$ to produce an intermediate having the formula

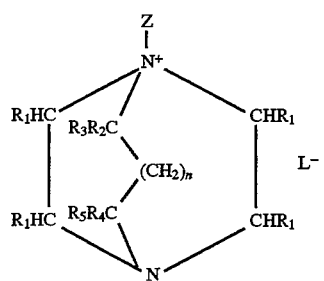

wherein L is a leaving group;

(b) exchanging the leaving group L, from step (a) with an anion X which is selected from the group consisting of fluorosulfate (SO$_3$ F$^-$), alkyl sulfates, perfluoroalkylsulfonates, arenesulfonates, alkylcarboxylates, perfluoro-alkylcarboxylates, tetrafluoroborate (BF$_4^-$), tetraphenylborate (Ph$_4^-$), hexafluorophosphate (PF$_6^-$), hexafluoroantimonate (SbF$_6^-$), perchlorate (ClO$_4^-$) and sulfate SO$_4$=; and (c) reacting the result from step (b) with molecular fluorine in the presence of a solvent that does not react substantially with fluorine and a fluoride scavenger that results in an X counter ion.

2. The process of claim 1 comprising the subsequent step of isolating the substituted-4-fluoro-1,4-diazoniabicyclo [2.2.2]octane salt from the reaction mixture.

3. The process of claim 1 wherein step (a) is conducted with 1,4-diazoniabicyclo[2.2.2]octane.

4. The process of claim 3 wherein the reactant compound is selected from the group consisting of methanesulfonyl chloride, phenylsulfonyl chloride, chlorophosphonic acid diethyl ester and diphenyl chlorophosphate.

5. The process of claim 1 wherein step (a) is conducted with 1,4-diazoniabicyclo[2.2.2]octane mono-N-oxide.

6. The process of claim 5 wherein the reactant compound is selected from the group consisting of fluoroboric acid, iodomethane and acetyl chloride.

7. The process of claim 1 wherein each of R$_1$, R$_2$, R$_3$, R$_4$ and R$_5$ is hydrogen.

8. The process of claim 1 wherein each R$_1$ is hydrogen and no more than one of R$_2$, R$_3$, R$_4$ and R$_5$ is other than hydrogen.

9. The process of claim 1 wherein each of R$_1$, R$_2$, R$_3$, R$_4$ and R$_5$ is hydrogen, benzyl, phenyl or a C$_1$–C$_4$ alkyl group.

10. The process of claim 1 wherein the X anion is tetrafluoroborate.

11. The process of claim I wherein the Z substituent is OH.

12. The process of claim 1 wherein the fluoride scavenger is a Lewis acid that readily reacts with fluoride.

13. The process of claim I wherein the fluoride scavenger is selected from the group consisting of aluminum trifluoride, antimony pentafluoride, arsenic pentafluoride, boron trifluoride, tris(trifluoromethyl)boron, tris (trifluorophenyl)boron, niobium pentafluoride, phosphorus pentafluoride, selenium trioxide, sulfur trioxide, tantalum pentafluoride, tellurium hexafluoride, titanium tetrafluoride, vanadium pentafluoride, zirconium tetrafluoride; salts and silyl derivatives of alkyl sulfonates, perfluoroalkanesulfonates, arenesulfonates, alkylcarboxylates and perfluoro alkylcarboxylates.

14. The process of claim 1 wherein the fluoride scavenger is present in an amount of from about 1 equivalent to about 5 equivalents based on the amount of the intermediate.

15. The process of claim 1 wherein the molecular fluorine is the $^{18}$F form.

16. The process of claim 1 wherein each of steps (a), (b) and (c) is independently conducted at a temperature of from about −40° C. to about 25° C.

17. The process of claim 1 wherein each of steps (a), (b) and (c) is independently conducted at a temperature of from about 10° C. to about 25° C.

18. The process of claim 1 wherein each of steps (a), (b) and (c) is independently conducted at a temperature of from about 15° C. to about 20° C.

19. The process of claim 1 wherein each of steps (a), (b) and (c) is independently conducted with a solvent of water, organic solvents and mixtures thereof.

20. The process of claim 19 wherein the organic solvent is selected from the group consisting of acetonitrile, propionitrile, trichlorofluoromethane, trichlorofluoroethane and mixtures thereof.

* * * * *

UNITED STATES PATENT AND TRADEMARK OFFICE
CERTIFICATE OF CORRECTION

PATENT NO : 5,631,372
DATED : May 20, 1997
INVENTOR(S) : Poss et al.

Page 1 of 3

It is certified that error appears in the above-identified patent and that said Letters Patent is hereby corrected as shown below:

Abstract, line 6, "$P_4$" should read -- $R_4$ --.

Column 1, line 25, "offluroinating" should read -- of fluorinating --.

Column 1, line 46, delete "[2.2.21]" and substitute -- [2.2.2] -- therefor.

Column 1, line 48, delete "employing" and substitute -- employ -- therefor.

Column 1, line 58, delete "ofenol" and substitute -- of enol -- therefor.

Column 3, line 15, delete "[2.2.21]" and substitute -- [2.2.2] -- therefor.

Column 3, line 22, delete "fiuoroboric" and substitute -- fluoroboric -- therefor.

Column 3, line 24, delete "[2.2.21]" and substitute -- [2.2.2] -- therefor.

Column 3, line 25, delete "oftriethylenediamine" and substitute -- of triethylenediamine -- therefor.

Column 3, line 28, delete "[2.2.21]" and substitute -- [2.2.2] -- therefor.

Column 4, line 64, delete "tetrafiuoro-borate" and substitute -- tetrafluoro-borate -- therefor.

Column 5, line 17, after "N," delete -- B --.

Column 7, line 15, delete "13,278" and substitute -- 13, 278 -- therefor.

UNITED STATES PATENT AND TRADEMARK OFFICE
CERTIFICATE OF CORRECTION

PATENT NO : 5,631,372
DATED : May 20, 1997
INVENTOR(S) : Poss et al.

It is certified that error appears in the above-identified patent and that said Letters Patent is hereby corrected as shown below:

Column 7, line 22, delete "flltrate" and substitute -- filtrate -- therefor.

Column 7, line 39, delete "mmool" and substitute -- mmol -- therefor.

Column 7, line 49, delete "tetrafiuoroborate" and substitute -- tetrafluoroborate -- therefor.

Column 7, line 65 delete "flitrate" and substitute -- filtrate -- therefor.

Column 8, line 53, delete "asteroid" and substitute -- a steroid -- therefor.

Column 9, line 10, delete "ofphenylurethan" and substitute -- of phenylurethan -- therefor.

Column 9, line 21, delete "ofalpha" and substitute -- of alpha-- therefor.

Column 9, line 38, delete "hydroxy2" and substitute -- hydroxy-2 -- therefor.

Column 10, line 37, delete "4-fiuoro" and substitute -- 4-fluoro -- therefor.

Column 10, line 42, delete "2-fiuorocyclohexanone" and substitute -- 2-fluorocyclohexanone -- therefor.

Claim 1, line 18, "$_{R4}$" should read -- $R_4$ --.

Claim 1, line 27, after "L—R,", delete -- R, --.

Claim 1, line 48, delete "$Ph_4^-$", and substitute -- $Ph_4B^-$ -- therefor.

Claim 1, line 50, delete "$ClO_4^-$" and substitute -- $ClO_4^-$ -- therefor.

UNITED STATES PATENT AND TRADEMARK OFFICE
CERTIFICATE OF CORRECTION

PATENT NO : 5,631,372
DATED : May 20, 1997
INVENTOR(S) : Poss et al.

It is certified that error appears in the above-identified patent and that said Letters Patent is hereby corrected as shown below:

Claim 1, line 62, delete "$SO_4=$" and substitute -- $SO_4^=$ -- therefor.

Claim 2, line 2, after "the", insert -- 1- --.

Claim 11, line 1, delete "I" and substitute -- 1 -- therefor.

Claim 13, line 1, delete "I" and substitute -- 1 -- therefor.

Signed and Sealed this

Thirtieth Day of November, 1999

Attest:

Attesting Officer

Q. TODD DICKINSON

Acting Commissioner of Patents and Trademarks